United States Patent
Dugger, III

[19]
[11] Patent Number: 5,955,098
[45] Date of Patent: Sep. 21, 1999

[54] BUCCAL NON POLAR SPRAY OR CAPSULE

[75] Inventor: Harry A. Dugger, III, Flemington, N.J.

[73] Assignee: Flemington Pharmaceutical Corp., Flemington, N.J.

[21] Appl. No.: 08/631,175

[22] Filed: Apr. 12, 1996

[51] Int. Cl.⁶ ...................................................... A61L 9/04
[52] U.S. Cl. .............................................. 424/435; 424/45
[58] Field of Search ........................................ 424/435, 45

[56] References Cited

U.S. PATENT DOCUMENTS

| 4,935,243 | 6/1990 | Borkan et al. . |
| 5,428,006 | 6/1995 | Bechgaard et al. ........................ 514/3 |

FOREIGN PATENT DOCUMENTS

| 0656206 | 6/1995 | European Pat. Off. . |
| 3338978 | 5/1984 | Germany . |
| 3246081 | 6/1984 | Germany . |
| 9304671 | 3/1993 | WIPO . |
| 9524893 | 9/1995 | WIPO . |

OTHER PUBLICATIONS

Rote Liste 1995, "Arzneimittelverzeichnis des BPI und VFA".

Primary Examiner—Carlos Azpuru
Attorney, Agent, or Firm—Omri M. Behr, Esq.

[57] ABSTRACT

A buccal aerosol spray or capsule using a non-polar solvent has now been developed which provides biologically active compounds for rapid absorption through the oral mucosa, resulting in fast onset of effect. The buccal aerosol spray of the invention comprises formulation I: propellant 50–95%, non-polar solvent 5–50%, active compound 0.001–15%, flavoring agent 00.05–5%. The soft bite gelatin capsule of the invention comprises formulation II: non-polar solvent 55–99.8%, emulsifier 0–20%, active compound 0.001–25%, and flavoring agent 0.05–5.0%.

18 Claims, 1 Drawing Sheet

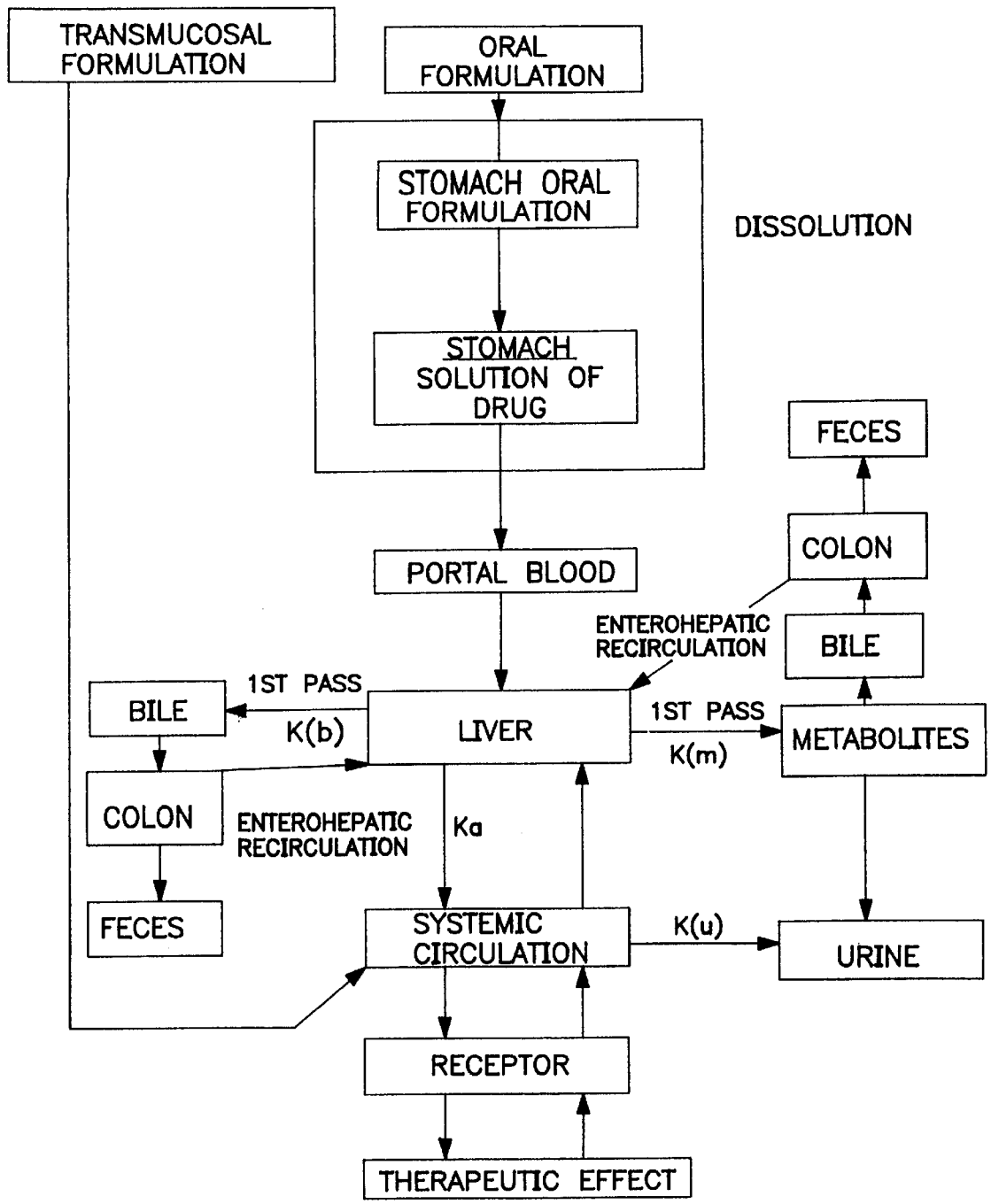

BUCCAL NON POLAR SPRAY OR CAPSULE

BACKGROUND OF THE INVENTION

It is known that certain biologically active compounds are better absorbed through the oral mucosa than through other routes of administration, such as through the stomach or intestine. However, formulations suitable for such administration by these latter routes present their own problems. For example, the biologically active compound must be compatible with the other components of the composition such as propellants, solvents, etc. Many such formulations have been proposed. For example, U.S. Pat. No. 4,689,233, Dvorsky et al., describes a soft gelatin capsule for the administration of the anti-coronary drug nifedipine dissolved in a mixture of polyether alcohols. U.S. Pat. No. 4,755,389, Jones et al., describes a hard gelatin chewable capsule containing nifedipine. A chewable gelatin capsule containing a solution or dispersion of a drug is described in U.S. Pat. No. 4,935,243, Borkan et al. U.S. Pat. No. 4,919,919, Aouda et al, and U.S. Pat. No. 5,370,862, Klokkers-Bethke, describe a nitroglycerin spray for administration to the oral mucosa comprising nitroglycerin, ethanol, and other components. An orally administered pump spray is described by Cholcha in U.S. Pat. No. 5,186,925. Aerosol compositions containing a hydrocarbon propellant and a drug for administration to a mucosal surface are described in U.K. 2,082,457, Su, U.S. Pat. No. 3,155,574, Silson et al., U.S. Pat. No. 5,011,678, Wang et al., and by Parnell in U.S. Pat. No. 5,128,132. It should be noted that these references discuss bioavailability of solutions by inhalation rather than through the membranes to which they are administered.

SUMMARY OF THE INVENTION

A buccal aerosol spray or soft bite gelatin capsule using a non-polar solvent has now been developed which provides biologically active compounds for rapid absorption through the oral mucosa, resulting in fast onset of effect.

The buccal aerosol spray compositions of the present invention, for transmucosal administration of a pharmacologically active compound soluble in a pharmacologically acceptable non-polar solvent comprising in weight % of total composition: pharmaceutically acceptable propellant 50–95%, non-polar solvent 5–50%, active compound 0.0025–40%, suitably additionally comprising, by weight of total composition a flavoring agent 0.05–5%. Preferably the composition comprises: propellant 55–85%, non-polar solvent 15–45%, active compound 0.025–20%, flavoring agent 0.1–2.5%; most suitably propellant 60–80%, non-polar solvent 19–32%, active compound 0.125–12.5%, flavoring agent 0.1–3.0%.

The soft bite gelatin capsules of the present invention for transmucosal administration of a pharmacologically active compound, at least partially soluble in a pharmacologically acceptable non-polar solvent, having charged thereto a fill composition comprising in weight % of total composition: non-polar solvent 30–99.8%, emulsifier 0–20%, active compound 0.0003–32%, provided that said fill composition contains less than 10% of water, suitably additionally comprising, by weight of the composition: flavoring agent 0.05–60%. Preferably, the soft bite gelatin capsule comprises: non-polar solvent 40–99.8%, emulsifier 0–15%, active compound 0.004–26%, flavoring agent 0.1–55%; most suitably: non-polar solvent 40–99.5%, emulsifier 0–10%, active compound 0.015–24.0%, flavoring agent 0.1–50%.

It is an object of the invention to coat the mucosal membranes either with extremely fine droplets of spray containing the active compounds or a solution or paste thereof from bite capsules.

It is also an object of the invention to administer to a mammalian in need of same preferably man, a predetermined amount of a biologically active compound by this method or from a soft gelatin bite capsule.

A further object is a sealed aerosol spray container containing a composition of the spray formulation, and a metered valve suitable for releasing from said container a predetermined amount of said composition.

As the propellant evaporates after activation of the aerosol valve, a mist of fine droplets is formed which contains solvent and active compound.

The propellant is a non-Freon material, preferably a $C_{3-8}$ hydrocarbon of a linear or branched configuration. The propellant should be substantially non-aqueous. The propellant produces a pressure in the aerosol container such that under expected normal usage it will produce sufficient pressure to expel the solvent from the container when the valve is activated but not excessive pressure such as to damage the container or valve seals.

The solvent is a non-polar hydrocarbon, preferably a $C_{7-18}$ hydrocarbon of a linear or branched configuration, its alcohols, fatty acid esters, and triglycerides, such as miglyol. The solvent must dissolve the active compound and be miscible with the propellant, i.e., solvent and propellant must form a single phase at 0–40° C. at a pressure range of 1–3 atm.

A further object is a soft gelatin bite capsule containing a composition of as set forth above. The formulation may be in the form of a viscous solution or paste containing the active compounds. Although solutions are preferred, paste fills may also be used where the active compound is not soluble or only partially soluble in the solvent of choice. Where water is used to form part of the paste composition, it should not exceed 10% thereof. (All percentages herein are by weight unless otherwise indicated.)

The non-polar solvent is chosen such that it is compatible with the gelatin shell and the active compound. The solvent preferably dissolves the active compound. However, other components wherein the active compound is not soluble or only slightly soluble may be used and will form a paste fill.

Soft gelatin capsules are well known in the art. See, for example, U.S. Pat. No. 4,935,243, Borkan et al., which is incorporated herein by reference for its teaching of such capsules. The capsules of the present invention are intended to be bitten into to release the low viscosity solution or paste therein, which will then coat the buccal mucosa with the active compounds. Typical capsules, which are swallowed whole or bitten and then swallowed, deliver the active compounds the stomach, which results in significant lag time before maximum blood levels can be achieved or subject the compound to a large first pass effect. Because of the enhanced absorption of the compounds through the oral mucosa and no chance of a first pass effect, use of the bite capsules of the invention will eliminate much of the lag time, resulting in hastened onset of biological effect. The shell of a soft gelatin capsule of the invention may comprise, for example: gelatine 50–75%, glycerine 20–30%, colorants 0.5–1.5%, water 5–10%, and sorbitol 2–10%.

The spray compositions of the invention are intended to be administered from a sealed, pressurized container. Unlike a pump spray, which allows the entry of air into the container after every activation, the aerosol container of the invention is sealed at the time of manufacture. The contents of the container are released by activation of a metered valve, will does not allow entry of atmospheric gasses with each activation. Such containers are commercially available.

BRIEF DESCRIPTION OF THE DRAWING

The FIGURE is a schematic diagram showing routes of absorption and processing of pharmacologically active substances in a mammalian system.

DESCRIPTION OF THE PREFERRED EMBODIMENTS

The preferred active compounds of the present invention are nicotine, clemastine, testosterone, estradiol, progesterone, fluoxetine, and piroxicam in their nonionized form or as the free base of the pharmaceutically acceptable salts thereof (provided, for the aerosol or spray compositions, they are soluble in the spray solvent), as well as, where appropriate the esters or triglycerides thereof. These compounds are soluble in the non-polar solvents of the invention at useful concentrations or can be prepared as pastes at useful concentrations. These concentrations may be less than the standard accepted dose for these compounds since there is enhanced absorption of the compounds through the oral mucosa. This aspect of the invention is especially important when there is a large (40–99.99%) First pass effect.

As propellants for the sprays, propane, N-butane, iso-butane, N-pentane, iso-pentane, and neo-pentane, and mixtures thereof may be used. N-butane and iso-butane, as single gases, are the preferred propellants. It is permissible for the propellant to have a water content of no more than 0.2%, typically 0.1–0.2%. (All percentages herein are by weight unless otherwise indicated.) It is also preferable that the propellant be synthetically produced to minimize the presence of contaminants which are harmful to the active compounds. These contaminants include oxidizing agents, reducing agents, Lewis acids or bases, and water. The concentration of each of these should be less than 0.1%, except that water may be as high as 0.2%.

Suitable solvents for the capsules include the spray solvents listed above, as well as $[C_2-C_{24}]$ fatty acid $C_2-C_6$ esters, including the triglycerides. Similarly, water is not a suitable solvent component in the spray compositions. When the capsule fill is a paste, other liquid components may be used instead of the above low molecular weight solvents. These include soya oil, corn oil, other vegetable oils, and $C_{7-18}$ hydrocarbons of a linear or branched configuration, and their alcohols and their fatty acid esters and triglycerides.

It is expected that some glycerin and water used to make the gelatin shell will migrate from the shell to the fill during the curing of the shell. Likewise, there may be some migration of components from the fill to the shell during curing and even throughout the shelf-life of the capsule. Therefore, the values given herein are for the compositions as prepared, it being within the scope of the invention that minor variations will occur.

The preferred flavoring agents are synthetic or natural oil of peppermint, oil of spearmint, citrus oil, fruit flavors, sweeteners (sugars, aspartame, saccharin, etc.), and combinations thereof.

The active substances include the active compounds selected from the group consisting of alkaloids, anti histamines, steroid hormones, non-steroidal anti-inflammatories, analgesics and anti-depressants, benzodiazepines, such as tamezepam.

Clemastine hydrogen fumarate is a known (Tavist®, Sandoz) anti-histamine. Both the spray and capsule of the invention advantageously coat the oral mucosa with an immediately available dose of clemastine which can be rapidly absorbed. This is highly desirable, as during an acute asthma attack.

Nicotine is a component of tobacco products which is considered addictive. Smokers wishing to stop smoking have a dual problem. First, is the addictive properties of nicotine itself. Second, is that the habit is associated with smoking activities, i.e., puffing, inhaling, etc. Both the spray and capsule of the invention dissociate these two problems. By presenting nicotine in a form which can be readily absorbed, the spray and capsule allow the smoker to temporarily continue nicotine use but terminate smoking. Once the habit of smoking is stopped, the former smoker can then be weaned off nicotine use, as by less frequent use and/or by use of a lower concentration spray or capsule. Advantageously, during this regimen, the user is exposed to none of the carcinogens present in tobacco smoke.

Testosterone is a hormone produced by gonadal cells. Testosterone, especially the esters thereof (e.g., acetate, propionate, enanthate, and cypionate), is used in the treatment of hypogonadism.

Estradiol is an estrogen steroid secreted from the ovaries. Estradiol, especially the esters thereof (e.g., diacetate, and benzoate), is used as estrogen replacement therapy, especially in post-menopausal women.

Progesterone is a hormone produced by the corpus luteum. Fluoxetine is an antidepressant also known as Prozac. Piroxicam is a known (Feldene®, Pfizer) anti-inflammatory.

The formulations of the present invention comprise an active compound or a pharmaceutically acceptable salt thereof. The term "pharmaceutically acceptable salts" refers to salts prepared from pharmaceutically acceptable non-toxic acids or bases including organic and inorganic acids or bases.

When an active compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucosamine, morpholine, piperazine, piperidine, polyamine resins, procaine, purine, theobromine, triethylamine, trimethylamine, tripropylamine, etc.

When an active compound of the present invention is basic, salts may be prepared from pharmaceutically acceptable non-toxic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tartaric acids.

In the discussion of methods of treatment herein, reference to the active compounds is meant to also include the pharmaceutically acceptable salts thereof. While certain formulations are set forth herein, the actual amounts to be administered to the mammal or man in need of same are to be determined by the treating physician.

The invention is further defined by reference to the following examples, which are intended to be illustrative and not limiting.

EXAMPLE 1

Clemastine Spray

A spray of the invention comprises the following formulation:

|  | Amount | Preferred Amount | Most-Preferred Amount |
|---|---|---|---|
| Propellant | 50–95% | 55–85% | 65–80% |
| Non-polar solvent | 5–50% | 15–45% | 20–35% |
| Clemastine Base | 0.12–10% | 0.25–6.25% | 0.25–5% |
| Flavoring agent | 0.05–3% | 0.1–2.5% | 0.2–2% |

It is particularly preferred to formulate the spray delivering 1.0 mg/activation formulation:

|  | Amount |
|---|---|
| Butane | 67% |
| Miglyol | 29.5% |
| Clemastine Base | 3.1% |
| Peppermint | 0.4% |

For delivery of 0.5 mg active substance, Clemastine Base 1.6%

EXAMPLE 2

Nicotine Spray

A spray of the invention comprises the following formulation:

|  | Amount | Preferred Amount | Most-Preferred Amount |
|---|---|---|---|
| Propellant | 50–95% | 55–85% | 65–80% |
| Non-polar solvent | 5–50% | 15–45% | 20–35% |
| Nicotine | 0.125–2.5% | 0.25–1.75% | 0.25–1.25% |
| Flavoring agent | 0.05–3% | 0.1–2.5% | 0.1–2.5% |

It is particularly preferred to formulate the spray delivering 0.5 mg/activation:

|  | Amount |
|---|---|
| Butane | 67% |
| Miglyol | 31.25% |
| Nicotine | 1.5% for 0.5 mg. |
| Peppermint | 0.25% |

For delivery of 0.4 mg active substance, Nicotine 1.25%.

EXAMPLE 3

Testosterone Spray

A spray of the invention comprises the following formulation:

|  | Amount | Preferred Amount | Most-Preferred Amount |
|---|---|---|---|
| Propellant | 50–95% | 55–85% | 65–80% |
| Non-polar solvent | 5–50% | 15–45% | 20–35% |
| Testosterone* | 0.125–25% | 2.5–20% | 5–12.5% |
| Flavoring agent | 0.05–3% | 0.1–2.5% | 0.1–2.5% |

*or esters thereof, preferably, the acetate, propionate, and enenthate esters

It is particularly preferred to formulate the spray delivering 4 mg/activation:

|  | Amount |
|---|---|
| Butane | 67% |
| Miglyol | 20.25% |
| Testosterone | 12.5% |
| Peppermint | 0.25% |

EXAMPLE 4

Estradiol Spray

A spray of the invention comprises the following formulation:

|  | Amount | Preferred Amount | Most-Preferred Amount |
|---|---|---|---|
| Propellant | 50–75% | 55–85% | 75–99% |
| Non-polar solvent | 25–50% | 15–45% | 20–35% |
| Estradiol* | 0.0025–2.5% | 0.025–1.5% | 0.125–1.0% |
| Flavoring agent | 0.05–3% | 0.1–2.5% | 0.1–2.5% |

*or esters thereof, preferably, the diacetate and benzoate esters

It is particularly preferred to formulate the spray:

|  | Amount |
|---|---|
| Butane | 67% |
| Miglyol | 32.4% |
| Estradiol | 0.31% |
| Peppermint | 0.25% |

EXAMPLE 5

Progesterone Spray

A spray of the invention comprises the following formulation:

|  | Amount | Preferred Amount | Most-Preferred Amount |
|---|---|---|---|
| Propellant | 50–75% | 55–85% | 65–80% |
| Non-polar solvent | 25–50% | 15–45% | 20–35% |

-continued

|  | Amount | Preferred Amount | Most-Preferred Amount |
|---|---|---|---|
| Progesterone | 0.0025–2.5% | 0.025–2.0% | 0.125–0.5% |
| Flavoring agent | 0.05–3% | 0.1–2.5% | 0.1–2.5% |

It is particularly preferred to formulate the spray delivering 0.32 mg/activation:

|  | Amount |
|---|---|
| Butane | 67% |
| Miglyol | 31.2% |
| Progesterone | 1.0% |
| Spearmint | 0.5% |

EXAMPLE 6

Clemastine Bite Capsule

A paste containing bite capsule of the invention comprises the following fill formulation:

|  | Amount | Preferred Amount | Most-Preferred Amount |
|---|---|---|---|
| Non-polar solvent | 75–99% | 90–98% | 85–99.5% |
| Emulsifier | 0–20% | 0–15% | 0–10% |
| Clemastine fumarate* | 0.0003–1.85% | 0.003–0.74% | 0.018–0.185% |
| Flavoring agent | 0.05–5% | 0.1–2.5% | 0.1–2.5% |

*as paste

It is particularly preferred to formulate the fill for the 1.34 mg capsule:

|  | Amount |
|---|---|
| Soya Oil | 91.4% |
| Lecithin | 5.88% |
| Clemastine fumarate | 0.50% for 1.34 mg. |
| Orange Aroma | 1.04% |
| Citron Oil | 0.81% |
| Na-Saccharine | 0.37% |

For delivery of 0.68 m active substance, Clemastine fumarate 0.25%.

EXAMPLE 7

Testosterone Bite Capsule

A bite capsule of the invention comprises the following fill formulation:

|  | Amount | Preferred Amount | Most-Preferred Amount |
|---|---|---|---|
| Non-polar solvent | 55–99% | 66–97% | 85–99.5% |
| Emulsifier/wetting agents | 0–20% | 0–15% | 0–10% |
| Testosterone* | 0.01–3.7% | 0.37–2.96% | 0.7–1.85% |
| Flavoring agent | 0.05–5% | 0.1–2.5% | 0.1–2.5% |

*or esters thereof, preferably, the acetate, propionate, and enenthate esters

It is particularly preferred to formulate the fill for 5 mg capsule:

|  | Amount |
|---|---|
| Miglyol | 90.1% |
| Lecithin | 5.88% |
| Testosterone | 1.8% |
| Orange Aroma | 1.04% |
| Citron Oil | 0.81% |
| Na-Saccharine | 0.37% |

EXAMPLE 8

Estradiol Bite Capsule

A bite capsule of the invention comprises the following fill formulation:

|  | Amount | Preferred Amount | Most-Preferred Amount |
|---|---|---|---|
| Non-polar solvent | 65–99% | 85–98% | 85–99.5% |
| Emulsifier/wetting agents | 0–20% | 0–15% | 0–10% |
| Estradiol* | 0.0003–1.85% | 0.003–0.74% | 0.018–0.185% |
| Flavoring agent | 0.05–5% | 0.1–2.5% | 0.1–2.5% |

*or esters thereof, preferably, the diacetate and benzoate esters

It is particularly preferred to formulate the fill for 0.5 mg capsule:

|  | Amount |
|---|---|
| Miglyol | 91.71% |
| Lecithin | 5.88% |
| Estradiol | 0.18 for 0.5 mg capsules |
| Orange Aroma | 1.04% |
| Citron Oil | 0.81% |
| Na Saccharine | 0.37% |

EXAMPLE 9

Progesterone Bite Capsule

A bite capsule of the invention comprises the following fill formulation:

|  | Amount | Preferred Amount | Most-Preferred Amount |
|---|---|---|---|
| Non-polar solvent | 55–99% | 75–98% | 85–99.5% |
| Emulsifier/wetting agents | 0–20% | 0–15% | 0–10% |
| Progesterone | 0.0003–3.7% | 0.0003–2.7% | 0.74–1.85% |
| Flavoring agent | 0.05–5% | 0.1–2.5% | 0.1–2.5% |

It is particularly preferred to formulate the fill for a 3 mg capsule:

|  | Amount |
|---|---|
| Miglyol | 91.83% |
| Lecithin | 5.88% |
| Progesterone | 1.11% |

-continued

| | Amount |
|---|---|
| Oil of Citron | 0.81% |
| Na-Saccharine | 0.37% |

EXAMPLE 10

Fluoxetine Bite Capsule

A bite capsule of the invention comprises the following fill formulation:

| | Amount | Preferred Amount | Most-Preferred Amount |
|---|---|---|---|
| Non-polar solvent | 75–99.8% | 75–99.8% | 85–99.5% |
| Emulsifier/wetting agents | 0–20% | 0–15% | 0–10% |
| Fluoxetine* HCl** | 0.018–9.25% | 0.37–3.7% | 0.74–3.7%** |
| Flavoring agent | 0.05–5% | 0.1–3% | 0.5–2.5% |

*If used as the free base, it will be a solution, at least in part
**As a paste.

It is particularly preferred to formulate the fill for a 5 mg capsule:

| | Amount |
|---|---|
| Soya Oil | 91.07% |
| Lecithin | 5.88% |
| Fluoxetine HCl | 1.85% |
| Peppermint | 1.2% |

EXAMPLE 11

Piroxicam Bite Capsule

A bite capsule of the invention comprises the following fill formulation:

| | Amount | Preferred Amount | Most-Preferred Amount |
|---|---|---|---|
| Non-polar solvent | 75–99.8% | 75–99.8% | 85–99.5% |
| Emulsifier/wetting agents | 0–20% | 0–15% | 0–10% |
| Piroxicam | 0.018–9.25% | 0.37–3.7% | 0.74–3.7% |
| Flavoring agent | 0.05–5% | 0.1–3% | 0.5–2.5% |

It is particularly preferred to formulate the fill for a 5 mg capsule:

| | Amount |
|---|---|
| Soya Oil | 91.07% |
| Lecithin | 5.88% |
| Piroxicam | 1.85% |
| Oil of Citron | 0.81% |
| Na Saccharine | 0.37% |

EXAMPLE 12

Nicotine 0.5 mg Bite Capsule

A bite capsule of the invention comprises the following fill formulation:

| | Amount | Preferred Amount | Most-Preferred Amount |
|---|---|---|---|
| Non-polar solvent | 30–99.8% | 35–99.8% | 40–99.5% |
| Emulsifier/wetting agents | 0–20% | 0–15% | 0–10% |
| Nicotine* | 0.018–0.74% | 0.037–0.37% | 0.37–0.20% |
| Flavoring agent | 0.05–60% | 0.1–55% | 0.5–50% |

*or as nicotine sulfate

It is particularly preferred to formulate the fill for a 0.5 mg capsule:

| | Amount |
|---|---|
| Soya Oil | 46.67% |
| Chocolate powder | 46.67% |
| Lecithin | 6.105% |
| Peppermint Oil | 0.185% |
| Na Saccharine | 0.185% |
| Nicotine | 0.185% |

EXAMPLE 13

Clemastine Fumarate with Phenylpropanolamine Hydrochloride Bite Capsule

A bite capsule of the invention comprises the following fill formulation:

| | Amount | Preferred Amount | Most-Preferred Amount |
|---|---|---|---|
| Non-Polar solvent | 65–99% | 50–98% | 70–98% |
| Clemastine fumarate* | 0.01–1.85% | 0.03–0.74% | 0.018–0.185% |
| Phenylpropanolamine HCl* | 1–30% | 1.5–20% | 1.8–10% |
| Flavoring agent | 0.05–5% | 0.1–2.5% | 0.1–2.5% |
| Emulsifier/Wetting Agent | 0–20% | 0–15% | 0–10% |

*Present as paste.

It is particularly preferred to formulate the composition fill for a clemastine fumarate 1.34 mg/25 mg phenylpropanolamine hydrochloride bite capsule:

| | Amount |
|---|---|
| Non-Polar Solvent: | |
| Soya | 82.20% |
| Lecithin | 5.88% |
| Clemastine fumarate | 0.50% |
| Phenylpropanolamine HCl | 9.20% |
| Orange aroma | 1.04% |
| Oil of Citrus | 0.81% |
| Na Saccharine | 0.37% |

EXAMPLE 14

Clemastine Fumarate/Pseudoephedrine Hydrochloride Bite Capsule

A bite capsule of the invention comprises the following fill formulation:

|  | Amount | Preferred Amount | Most-Preferred Amount |
|---|---|---|---|
| Non-Polar solvent | 50–95% | 55–90% | 60–85% |
| Emulsifier/wetting agent | 0–20% | 0–15% | 0–10% |
| Clemastine fumarate* | 0.01–1.85% | 0.03–0.74% | 0.05–0.185% |
| Pseudoephedrine HCl* | 3–30% | 5–25% | 10–23% |
| Flavoring agent | 0.05–5% | 0.1–2.5% | 0.1–2.5% |

*Present as paste.

It is particularly preferred to formulate the composition fill for a 1.34 mg clemastine fumarate/60 mg pseudoephedrine HCl capsule:

|  | Amount |
|---|---|
| Non-Polar Solvent: |  |
| Soya | 69.18% |
| Lecithin | 5.88% |
| Clemastine fumarate | 0.50% |
| Phenylpropanolamine HCl | 22.22% |
| Orange aroma | 1.04% |
| Oil of Citrus | 0.81% |
| Na Saccharine | 0.37% |

What is claimed is:

1. A buccal aerosol spray composition for transmucosal administration of a pharmacologically active compound soluble in a pharmacologically acceptable non-polar solvent comprising in weight % of total composition: pharmaceutically acceptable propellant selected from the group consisting of $C_3$ Through 8 hydrocarbons of linear or branch configuration 50–95%, non-polar solvent 5–50%, active 0.0025–40% wherein the active compound is selected from the group consisting of alkaloids. anti-histamines, steroid hormones, non-steroidal and anti-inflammatories, analgesics, benzediazepines and anti-depressants.

2. The composition of claim 1 additionally comprising, by weight of total composition: flavoring agent 0.05–5%.

3. The composition of claim 2 comprising: propellant 55–85%, non-polar solvent 15–45%, active compound 0.025–20%, flavoring agent 0.1–2.5%.

4. The composition of claim 2 comprising: propellant 60–80%, non-polar solvent 19–32%, active compound 0.125–12.5%, flavoring agent 1–2%.

5. The composition of claim 1 wherein the propellant is propane, N-butane, iso-butane, N-pentane, iso-pentane, or neo-pentane, and mixtures thereof.

6. The composition of claim 1 wherein the propellant is N-butane or iso-butane and has a water content of no more than 0.2% and oxidizing agents, reducing agents, and Lewis acids or bases content in a concentration of less than 0.1%.

7. The composition of claim 1 wherein the solvent is a selected from the group consisting of ($C_2$–$C_{24}$) fatty acid ($C_2$–$C_6$) esters, $C_7$–$C_{18}$ hydrocarbons of a linear or branched configuration, and $C_2$–$C_8$ alkanoyl esters, and triglycerides of the alcohols thereof.

8. The composition of claim 1 wherein the solvent is miglyol.

9. The composition of claim 1 wherein the active compound is selected from the group consisting of nicotine, clemastine, testosterone, estradiol, progesterone, tamezepam, fluoxetine, and piroxicam in their nonionized form or as the free base of the pharmaceutically acceptable salts thereof.

10. The composition of claim 2 wherein the flavoring agents are selected from the group consisting of synthetic or natural oil of peppermint, oil of spearmint, citrus oil, fruit flavors, sweeteners and combinations thereof.

11. The composition of claim 1 of the formulation: propellant 50–95%, non-polar solvent 5–50%/, clemastine base 0.12–10%, flavoring agent 0.05–3%.

12. The composition of claim 1 of the formulation: propellant 50–95%, non-polar solvent 5–50%, nicotine 0.125–2.5%, flavoring agent 0.05–3%.

13. The composition of claim 1 of the formulation: propellant 50–95%, non-polar solvent 5–50%, a member selected from the group consisting of testosterone and the pharmaceutically acceptable esters thereof 0.125–25%, flavoring agent 0.05–3%.

14. The composition of claim 1 of the formulation: propellant 50–75%, non-polar solvent 25–50%, a member selected from the group consisting of estradiol and the pharmaceutically acceptable esters thereof 0.0025–2.5%, flavoring agent 0.05–3%.

15. The composition of claim 1 of the formulation: propellant 50–75%, non-polar solvent 25–50%, a member selected from the group consisting of progesterone and the pharmaceutically acceptable esters thereof 0.025–2.5%, flavoring agent 0.05–3%.

16. A method of administering a pharmacologically active compound to a mammal in needed of same, by spraying the oral mucosa of said mammal with a composition of claim 1.

17. The method of claim 16 wherein the amount of spray administered is predetermined.

18. A sealed aerosol spray container containing a composition of claim 1 and a metered valve suitable for releasing from said container a predetermined amount of said composition.

* * * * *